(12) United States Patent
Liu

(10) Patent No.: US 11,666,103 B2
(45) Date of Patent: Jun. 6, 2023

(54) ANTI-CONDENSATION MODULE AND ELECTRONIC CIGARETTE COMPRISING THE SAME

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 342 days.

(21) Appl. No.: 16/930,303

(22) Filed: Jul. 15, 2020

(65) Prior Publication Data
US 2022/0015458 A1 Jan. 20, 2022

(51) Int. Cl.
*A24F 40/40* (2020.01)
*A24F 47/00* (2020.01)
*A61M 15/06* (2006.01)
*A24C 5/01* (2020.01)
*A24F 7/00* (2006.01)

(52) U.S. Cl.
CPC .............. *A24F 47/00* (2013.01); *A24C 5/01* (2020.01); *A24F 7/00* (2013.01); *A24F 40/40* (2020.01); *A61M 15/06* (2013.01)

(58) Field of Classification Search
CPC .. A24F 47/00; A24F 7/00; A24F 40/40; A24F 40/10; A24F 40/44; A24C 5/01; A61M 15/06; A61M 11/00
See application file for complete search history.

(56) References Cited

U.S. PATENT DOCUMENTS

| 10,334,887 B1* | 7/2019 | Qiu ........................ A24F 40/49 |
| 2015/0359261 A1* | 12/2015 | Li et al. .................. A24F 40/44 |
| | | 392/394 |
| 2017/0295846 A1* | 10/2017 | Liu ........................ A24F 40/40 |
| 2018/0303162 A1* | 10/2018 | Zhang et al. .......... A24F 40/485 |

FOREIGN PATENT DOCUMENTS

| CN | 202385728 U | * | 8/2012 | ............. A24F 40/50 |
| WO | WO-2019028742 A1 | * | 2/2019 | ........... A24F 40/485 |
| WO | WO-2021142740 A1 | * | 1/2020 | ............. A24F 40/42 |

OTHER PUBLICATIONS

Zhou, Xue-wu, "Built-in electronic cigarette atomizer" (PE2E machine translation) (Year: 2012).*
Qiu, Weihua et al., "Atomizer heads, atomizers, and electronic cigarettes" (EPO Patent Translate, machine translation) (Year: 2019).*
Zhou, Xuewu, "Electronic cigarette vaporizer and electronic cigarette" (EPO Patent Translate, machine translation) (Year: 2020).*

* cited by examiner

*Primary Examiner* — Kelly M Gambetta
*Assistant Examiner* — Katherine A Will
(74) *Attorney, Agent, or Firm* — Matthias Scholl P.C.; Matthias Scholl

(57) ABSTRACT

An anti-condensation module including an atomizing cylinder, a first piece of cotton, a ceramic atomization core disposed in the atomizing cylinder, and a second piece of cotton. The first piece of cotton and the second piece of cotton are disposed on two ends of the ceramic atomization core, respectively, configured to adsorb condensates on the two ends of the ceramic atomization core, respectively.

4 Claims, 3 Drawing Sheets

ANTI-CONDENSATION MODULE AND ELECTRONIC CIGARETTE COMPRISING THE SAME

BACKGROUND

The disclosure relates to an anti-condensation module and an electronic cigarette comprising the same.

Known electronic cigarettes comprise no anti-condensation device. When encountering cold air, the vapor resulting from the atomization of the e-liquid tends to form condensates, which may block the air channel of the electronic cigarettes.

SUMMARY

The disclosure provides an anti-condensation module comprising an atomizing cylinder, a first piece of cotton, a ceramic atomization core disposed in the atomizing cylinder, and a second piece of cotton. The first piece of cotton and the second piece of cotton are disposed on two ends of the ceramic atomization core, respectively, configured to adsorb condensates on the two ends of the ceramic atomization core, respectively.

The anti-condensation module further comprises a supporting seat disposed in the atomizing cylinder; the ceramic atomization core is fixedly connected to the supporting seat.

The disclosure also provides an electronic cigarette, comprising the anti-condensation module.

The electronic cigarette further comprises a mouthpiece, a joint, a shell, and a pneumatic switch; the pneumatic switch is hollow; in use, an air flow enters the electronic cigarette from a charging port disposed on a bottom of the shell and drives the pneumatic switch to work, then passes through the joint and the atomizing cylinder, and exits from the mouthpiece.

The electronic cigarette further comprises a first silica gasket, a battery, a sleeve tube, a second silica gasket, a control plane, a support, and a decorative sheet; the second silica gasket is disposed on the pneumatic switch; when the air flow passes through the pneumatic switch, the pneumatic switch senses the air flow and controls the output of the control plane; the control plane is disposed on the support; the battery is disposed on the control plane; the battery is disposed in the sleeve tube; the sleeve tube is disposed in the shell; the decorative sheet is attached to a bottom of the shell; and the first silica gasket is disposed in the shell.

The first piece of cotton and the second piece of cotton are disposed on two ends of the ceramic atomization core, respectively, configured to adsorb condensates on the two ends of the ceramic atomization core, respectively, thereby preventing the condensates from blocking the air channel.

DETAILED DESCRIPTION

To further illustrate, embodiments detailing an electronic cigarette are described below. It should be noted that the following embodiments are intended to describe and not to limit the disclosure.

Figure 1:
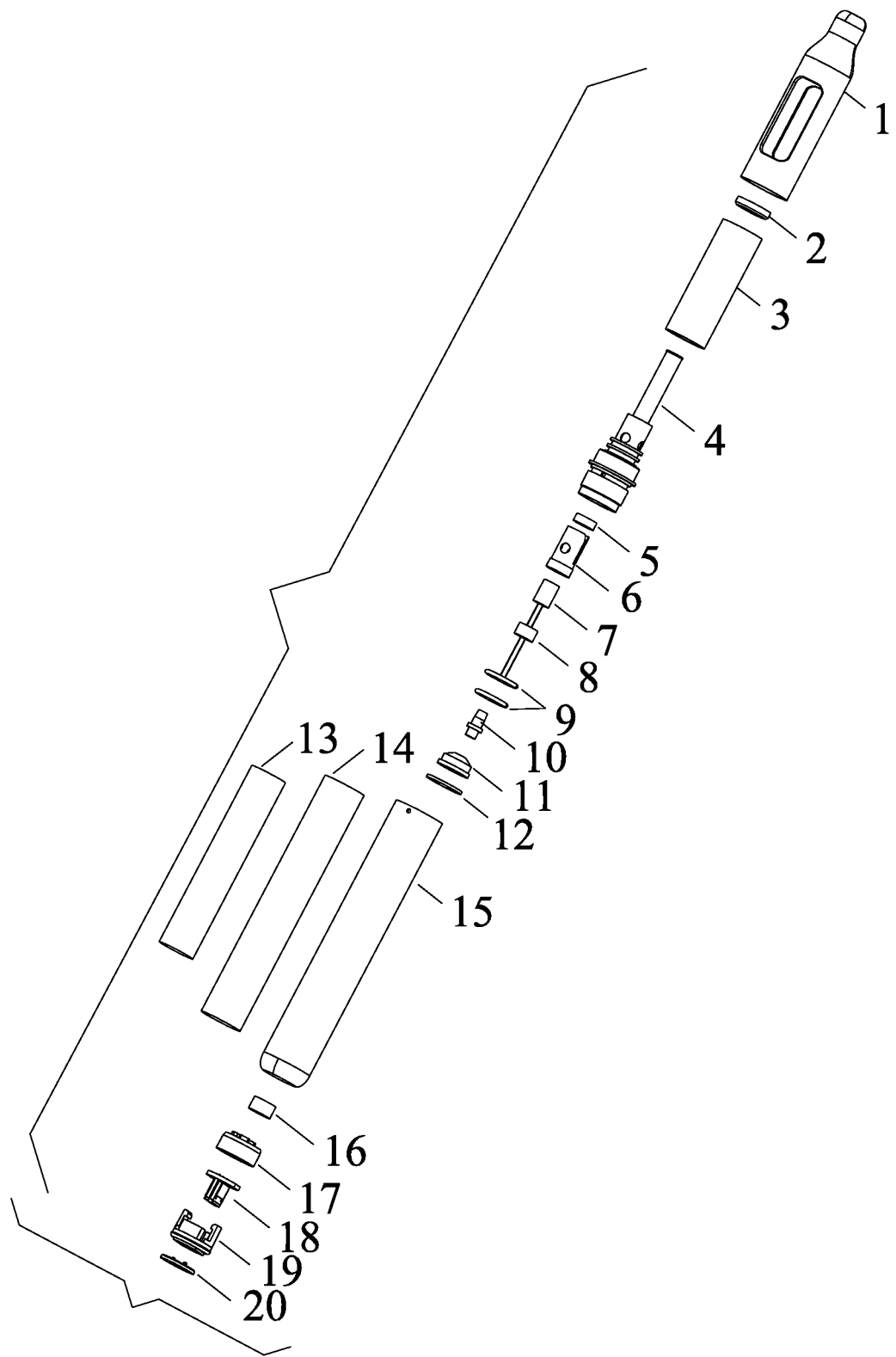
FIG. 1 is an exploded view of an electronic cigarette according to one embodiment of the disclosure.
Figure 2:
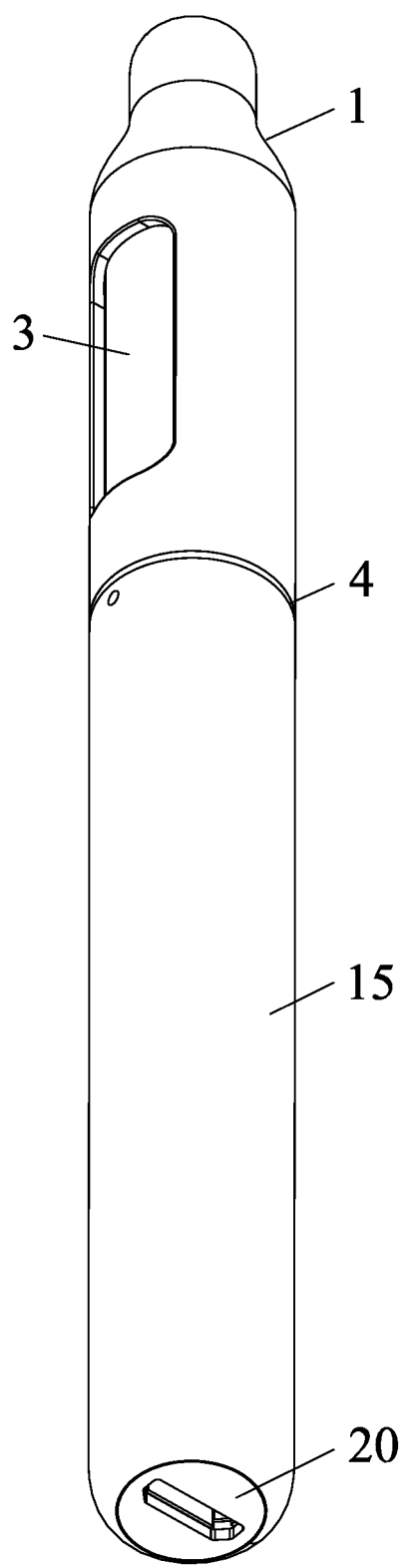
FIG. 2 is a schematic diagram of an electronic cigarette according to one embodiment of the disclosure.
Figure 3:
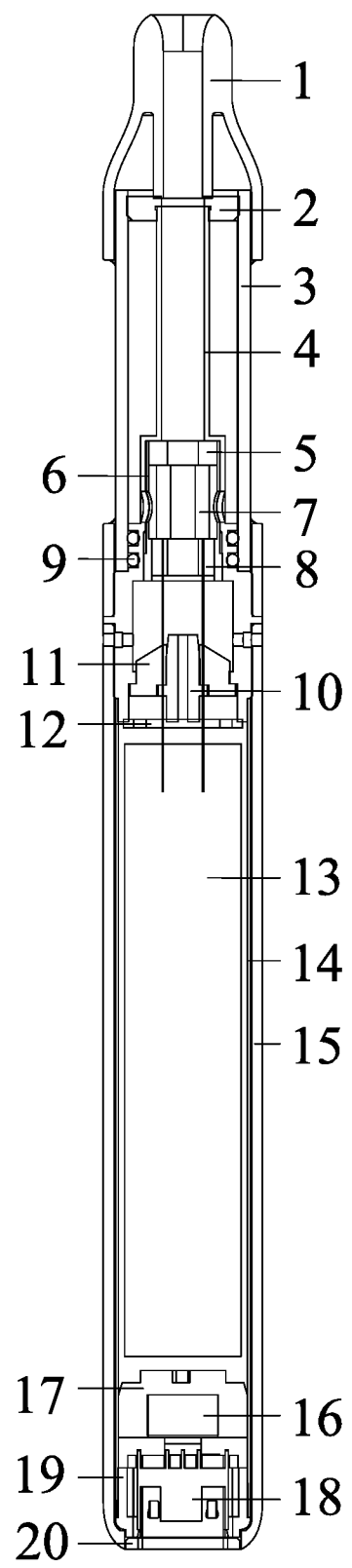
FIG. 3 is a sectional view of an electronic cigarette according to one embodiment of the disclosure.

As shown in FIGS. 1-3, an electronic cigarette comprises a mouthpiece 1, a first seal ring 2, a glass tube 3, an atomizing cylinder 4, a first piece of cotton 5, a supporting seat 6 disposed in the atomizing cylinder, a ceramic atomization core 7 disposed in the atomizing cylinder 4, a second piece of cotton 8, a second seal ring 9, a joint 10, an insulation ring 11, a first silica gasket 12, a battery 13, a sleeve tube 14, a shell 15, a pneumatic switch 16, a second silica gasket 17, a control plane 18, a support 19, and a decorative sheet 20. The second silica gasket 17 is disposed on the pneumatic switch 16; the control plane 18 is welded on the pneumatic switch 16. When the air flow passes through the pneumatic switch 16, the pneumatic switch 16 senses the air flow and controls the output of the control plane 18; the control plane 18 is disposed on the support 19; the battery 13 is disposed on the control plane 18; the battery 13 is disposed in the sleeve tube 14; the sleeve tube 14 is disposed in the shell 15; the decorative sheet 20 is attached to a bottom of the shell 15; and the first silica gasket 12 is disposed in the shell 15. The first piece of cotton 5 and the second piece of cotton 8 are disposed on two ends of the ceramic atomization core 7, respectively, configured to adsorb condensates on the two ends of the ceramic atomization core 7, respectively. The insulation ring 11 is disposed in the atomizing cylinder 4 to separate the positive and negative poles. The joint 10 is disposed in the insulation ring 11. The atomizing cylinder 4 is disposed in the glass tube 3. The first seal ring 2 and the second seal ring 9 are disposed on two ends of the glass tube 3, respectively, thereby sealing the two ends of the glass tube. The glass tube 3 is disposed in the cavity of the mouthpiece 1. The mouthpiece 1 is fixedly connected to the shell 15.

The following advantages are associated with the electronic cigarette of the disclosure.

1. The first piece of cotton and the second piece of cotton are disposed on two ends of the ceramic atomization core, respectively, configured to adsorb condensates on the two ends of the ceramic atomization core, respectively, thereby preventing the condensates from blocking the air channel.

2. The air channel of the electronic cigarette is straight, so that the air flow enters the electronic cigarette from the bottom of the shell and drives the pneumatic switch to work, then passes through the air channel, and exits from the top of the electronic cigarette.

It will be obvious to those skilled in the art that changes and modifications may be made, and therefore, the aim in the appended claims is to cover all such changes and modifications.

What is claimed is:

1. An electronic cigarette, comprising: a mouthpiece, a glass tube, a supporting seat, an atomizing cylinder, a first piece of cotton, a ceramic atomization core configured for atomizing e-liquid, and a second piece of cotton;

wherein:
the glass tube is disposed in a cavity of the mouthpiece;
the atomizing cylinder has a hollow cylindrical part, and is disposed in the glass tube;
the supporting seat is disposed in the hollow cylindrical part;
the first piece of cotton, the ceramic atomization core, and the second piece of cotton are disposed in a cavity of the supporting seat;
the first piece of cotton and the second piece of cotton are disposed on and are in contact with two ends of the ceramic atomization core, respectively, configured to adsorb condensates on the two ends of the ceramic atomization core, respectively.

2. The device of claim 1, wherein the supporting seat has a cylindrical shape, and has a hole on a side wall; the ceramic atomization core is fixedly connected to the supporting seat.

3. The electronic cigarette of claim 1, wherein the electronic cigarette further comprises a joint, a shell, and a pneumatic switch; wherein the pneumatic switch is hollow; and when in use, an air flow enters the electronic cigarette from a bottom of the shell and drives the pneumatic switch to work, then passes through the joint and the atomizing cylinder, and exits from the mouthpiece.

4. The electronic cigarette of claim 3, wherein the electronic cigarette further comprises a first silica gasket, a battery, a sleeve tube, a second silica gasket, a control plane, a support, and a decorative sheet; wherein the second silica gasket is disposed on the pneumatic switch, and when the air flow passes through the pneumatic switch, the pneumatic switch senses the air flow and controls the output of the control plane; and wherein the control plane is disposed on the support; the battery is disposed on the control plane; the battery is disposed in the sleeve tube; the sleeve tube is disposed in the shell; the decorative sheet is attached to a bottom of the shell; and the first silica gasket is disposed in the shell.

* * * * *